US012319945B2

(12) United States Patent
Poechlauer et al.

(10) Patent No.: US 12,319,945 B2
(45) Date of Patent: Jun. 3, 2025

(54) SINGLE STEP BIOCATALYTIC AMIDATION

(71) Applicant: PATHEON AUSTRIA GMBH & CO KG, Linz (AT)

(72) Inventors: Peter Poechlauer, Linz (AT); Philipp Selig, Linz (AT); Christopher Zinganell, Linz (AT); Julia Pitzer, Graz (AT); Anton Glieder, Hofstatten an der Raab (AT); Wolfgang Kroutil, Graz (AT); Kerstin Steiner, Graz (AT)

(73) Assignee: PATHEON AUSTRIA GMBH & CO KG, Linz (AT)

( * ) Notice: Subject to any disclaimer, the term of this patent is extended or adjusted under 35 U.S.C. 154(b) by 297 days.

(21) Appl. No.: 17/415,856

(22) PCT Filed: Dec. 3, 2019

(86) PCT No.: PCT/EP2019/083541
§ 371 (c)(1),
(2) Date: Jun. 18, 2021

(87) PCT Pub. No.: WO2020/126484
PCT Pub. Date: Jun. 25, 2020

(65) Prior Publication Data
US 2022/0073958 A1   Mar. 10, 2022

(30) Foreign Application Priority Data
Dec. 18, 2018   (EP) ..................... 18213434

(51) Int. Cl.
C12P 13/02       (2006.01)
C12N 9/20        (2006.01)

(52) U.S. Cl.
CPC ....... *C12P 13/02* (2013.01); *C12Y 301/01003* (2013.01)

(58) Field of Classification Search
None
See application file for complete search history.

(56) References Cited

FOREIGN PATENT DOCUMENTS

EP        0570244 A1     11/1993

OTHER PUBLICATIONS

Lanigan et al., "Direct amidation of unprotected amino acids using B(OCH2CF3)3", Chem. Comm. 52:8846-8849, 2016 (Year: 2016).*
Conde et al., Journal of Molecular Catalysis B: Enzymatic 7:299-306, 1999 (Year: 1999).*
Singh et al., Curr. Protein Pept. Sci. 18:1-11, 2017 (Year: 2017).*
Zhang et al., Structure 26:1474-1485, 2018 (Year: 2018).*
Liu et al., J. Biol. Chem. 286:11211-11217, 2011 (Year: 2011).*
Vijayakumar et al., "Lipase catalyzed synthesis of L-alanyl, L-leucyl and L-phenylalanyl esters of D-glucose using unprotected amino acids", Biotechnol. Lett. 26:1323-1328, 2004 (Year: 2004).*
Conde et al., Tetrahedron 53:11745-11752, 1997 (Year: 1997).*
Lundberg H. et al., "Catalytic amide formation from non-activated carboxylic acids and amines", Chemical Society Reviews, vol. 43, No. 8, Jan. 1, 2014 (Jan. 1, 2014), p. 2714.
Pitzer J. et al., "Amides in Nature and Biocatalysis," J. of Biotechnol. 235, 32-46 (2016).
Tachiki et al., "γ-Glutamyl Transfer Reactions by Glutaminase from Pseudomonas nitroreducens IFO 12694 and Their Application for the Syntheses of Theanine and γ-Glutamylmethylamide," Biosci. Biotechnol. Biochem. 62(7), 1279-1283 (1998).
Nuijens, T. et al., "Enzymatic C-Terminal Amidation of Amino Acids and Peptides," Tetrahedron Lett. 53, 3777-3779 (2012).
Litjens M.J.J., et al., "Exploration of Lipase-Catalyzed Direct Amidation of Free Carboxylic Acids with Ammonia in Organic Solvents," Tetrahedron 55, 12411-12418 (1999).
Goswami A., et al., "Enzymatic Strategies and Biocatalysts for Amide Bond Formation: Tricks of the Trade Outside of the Ribosome," Mol. Biosyst. Feb. 20, 2015; 11(2): 338-353.
Yang B. et al., "Amidation of Amines With Esters Catalyzed by Candida Antarctica Lipase (CAL)," Indian J. Chem. 44B, Jun. 2005, 1312-1316.
Peng, Xiang-Qian, "Improved Thermostability of Lipase B from Candida Antarctica by Directed Evolution and Display on Yeast Surface," Appl Biochem Biotechnol (2013) 169:351-358.
Vogl et al., "A Toolbox of Diverse Promoters Related to Methanol Utilization: Functionally Verified Parts for Heterologous Pathway Expression in Pichia pastoris," ACS Synthetic Biology, 5(2), pp. 172-186 (2016).
International Search Report and Written Opinion mailed Mar. 6, 2020 for PCT/EP2019/083541, 17 pages.
International Preliminary Report on Patentability mailed Jun. 16, 2021 for PCT/EP2019/083541, 7 pages.
Den Dunnen, et al., "HGVS Recommendations For The Description of Sequence Variants: 2016 update," Hum. Mutat. 25: 37: 564-569 (2016).
Uppenberg, Jonas, et al., "The Sequence, Crystal Structure Determination and Refinement of Two Crystal Forms of Lipase B from Candida Antarctica." Structure, Apr. 15, 1994; 2:293-308, 16 pages.
Conde et al., "Regioselective Lipase-Catalyzed Synthesis of L-Glutamic a-Monoamide Derivatives. Effect of the N-Blocking Group," Tetrahedron 53, No. 34: 11745-11752, 1997.

* cited by examiner

*Primary Examiner* — David Steadman
(74) *Attorney, Agent, or Firm* — Raymond G. Arner; Pierce Atwood LLP

(57) ABSTRACT

The present invention relates to a process for biocatalytic amidation of non-protected amino acids comprising the step of contacting a non-protected amino acid with an ammonia source in the presence of an organic solvent and an enzyme.

8 Claims, 8 Drawing Sheets
Specification includes a Sequence Listing.

Fig. 13

SEQ ID NO: 1

```
           10         20         30         40         50
   LPSGSDPAFS QPKSVLDAGL TCQGASPSSV SKPILLVPGT GTTGPQSFDS
           60         70         80         90        100
   NWIPLSXQLG YTPCWISPPP FMLNDTQVNT EYMVNAITXL YAGSGNNKLP
          110        120        130        140        150
   VLTWSQGGLV AQWGLTFFPS IRSKVDRLMA FAPDYKGTVL AGPLDALAVS
          160        170        180        190        200
   APSVWQQTTG SALTTALXNA GGLTQIVPTT NLYSATDEIV QPQVSNSPLD
          210        220        230        240        250
   SSYLFNGKNV QAQAVCGPLF VIDHAXSLTS QFSYVVGRSA LRSTTGQARS
          260        270        280        290        300
   ADYGITDCNP LPANDLTPEQ KVAAAALLAP AAAAIVAGPK QNCEPDLMPY
          310        317
   ARPFAVGKRT CSGIVTP
```

SINGLE STEP BIOCATALYTIC AMIDATION

RELATED APPLICATIONS

This application claims priority under 35 U.S.C. § 371 to International Patent Application No. PCT/EP2019/083541 filed Dec. 3, 2019, which claims priority to European Patent Application No. 18213434.6 filed on Dec. 18, 2018, the disclosure of each of which is incorporated by reference herein in its entirety.

SEQUENCE LISTING

The instant application incorporates by reference the Sequence Listing in the ASCII text file filed Jun. 18, 2021, entitled "DPX-055US01-Sequence Listing", which file was created on Jun. 17, 2021, the size of which file is 3,100 bytes.

FIELD OF THE INVENTION

The present invention relates to the field of biocatalytic amidation. Specifically, the present invention relates to a process for biocatalytic amidation of non-protected amino acids comprising the step of contacting a non-protected amino acid with an ammonia source in the presence of an organic solvent and an enzyme.

BACKGROUND ART

The amide functionality constitutes the essential backbone of numerous natural as well as synthetic structures. Its occurrence especially in proteins, pharmaceuticals and polymers makes it an attractive target for the development of chemical as well as biocatalytic processes. Numerous strategies for amide synthesis exist in both fields (Lundberg H. et al., Chem. Soc. Rev. 43, 2714 (2014), Pitzer J. et al., J. of Biotechnol. 235, 32-46 (2016)). The importance and the requirement of improvements in amide formation processes were underlined in a voting of the ACS GCI Pharmaceutical Roundtable. Amide formation avoiding poor atom economy reagents was selected as the reaction with the highest interest of pharmaceutical companies for better and greener reagents.

Previous efforts were mainly focused on amide formation from activated species, e.g., esters, or from lipophilic substrates, such as long chain fatty acids and amines. Amidation of octanoic acid was e.g. performed via the ester intermediate, since direct ammonolysis led to the formation of salts instead of the desired octanamide. Solvent free systems were applied for the enantioselective amidation of aliphatic acids with rac 2-ethylhexyl amine. In addition to amidation reactions, amide formation can also be performed biocatalytically by using e.g. gamma-glutamyl transfer reactions (Tachiki et al., Biosci. Biotechnol. Biochem. 62(7), 1279-1283 (1998)).

Furthermore, selective enzymatic kinetic resolution of various primary amines was reported for the amidation of carboxylic esters and acids with CalB in hexane. The most straightforward way, the reaction of carboxylic acids with ammonia, was rarely achieved. Cbz-protected amino acids and peptides, as well as peptides with a free N-terminal amine have been successfully converted to the amide with the protease Alcalase CLEA, which is specific towards alpha-carboxylic acids (Nuijens, T. et al., Tetrahedron Lett. 53, 3777-3779 (2012)). Further, Cbz-protected amino acids and peptides have been converted to the amide with the lipase CalB using ammonium salts or ammonia (Nuijens, T. et al., Tetrahedron Lett. 53, 3777-3779 (2012)).

Because of the low solubility of unprotected amino acids in organic solvents, their direct amidation with CalB is not expected to be feasible (Litjens M. J. J., et al., Tetrahedron 55, 12411-12418 (1999)).

Considering the principles of green chemistry, including atom efficiency and waste prevention, the avoidance of derivatization steps is highly desirable. Yet biocatalytic amidation of underivatized amino acids has not been accomplished. Thus, there is still the need for an improved method for direct biocatalytic amidation of unprotected amino acids.

SUMMARY OF INVENTION

Therefore it is the object of the present invention to provide an improved method for direct biocatalytic amidation of unprotected amino acids.

The object is solved according to the invention by providing a single step method for biocatalytic amidation of unprotected amino acids.

Thus, the present invention relates to a process for biocatalytic amidation of non-protected amino acids comprising the step of contacting a non-protected amino acid with an ammonia source in the presence of an organic solvent and an enzyme.

A further embodiment of the invention relates to the process as described herein, wherein the enzyme is a lipase.

A further embodiment of the invention relates to the process as described herein, wherein the lipase is *Candida antarctica* lipase B (CalB) or a variant thereof.

A further embodiment of the invention relates to the process as described herein, wherein the CalB variant comprises the amino acid substitutions T57A/A89T/G226R/R168K with reference to the numbering of SEQ ID NO:1.

A further embodiment of the invention relates to the process as described herein, wherein the enzyme is immobilized.

A further embodiment of the invention relates to the process as described herein, wherein the ammonia source is ammonia ($NH_3$), ammonium carbamate, ammonium carbonate, benzylamine, ethanolamine, hexylamine, 2-phenylethylamine, or 3-phenylpropylamine, or any mixtures thereof.

A further embodiment of the invention relates to the process as described herein, wherein the organic solvent is selected from the group consisting of dioxane, 2-methyl-2-butanol, and t-butanol, or from ionic liquids.

A further embodiment of the invention relates to the process as described herein, wherein the unprotected amino acid is L-proline.

One embodiment of the invention relates to the process as described herein, carried out at a temperature in the range of 60 to 80° C.

A further embodiment of the invention relates to the process as described herein, wherein ammonia is comprised in the organic solvent.

A further embodiment of the invention relates to the process as described herein, wherein the water content in the reaction media is below 1.0 v/v %, or below 0.5 v/v %.

A further embodiment of the invention relates to the process as described herein, wherein the process is performed in batch or continuous mode.

One embodiment of the invention relates to the process as described herein, wherein the unprotected amino acid is provided in an amount of 0.01-1.0% w and the enzyme is provided in an amount of 0.01-1.0% w.

BRIEF DESCRIPTION OF DRAWINGS

FIG. 13 depicts the amino acid sequence of CalBopt.

DESCRIPTION OF EMBODIMENTS

The aim of the present invention is to develop a one-pot process for biocatalytic amidation of non-protected amino acids with high conversions, which is also applicable at large scale. One of the main challenges is the low solubility of highly polar, charged substrates in lipophilic solvents. Reaction media in which the substrate is highly soluble, e.g., water or methanol, have to be avoided due to the reverse hydrolytic reaction and issues with enzyme inhibition. Frequently recommended options for water-free, polar environments are ionic liquids and deep eutectic solvents.

The improved process as described herein is suitable for carboxylic acids bearing an amino moiety, specifically for amino acids, wherein the amino group is not covered by a protecting group such as benzyl carbamates (Cbz), tert-butoxycarbonyl (Boc), or fluorenylmethyloxycarbonyl (Fmoc). Preferably, it is a non-protected amino acid, more preferably it is non-protected L-proline. Optionally, the method as described herein may also be suitable for non-protected carboxylic acid such as non-fatty carboxylic acids, e.g., phenylpropanoic acid, cyclopentanoic acid.

As used herein, the term "non-protected amino acid" refers to an amino acid wherein neither the alpha-amino group, nor any side chain functionality is protected by a protecting group such as benzyl carbamates (Cbz), tert-butoxycarbonyl (Boc), or fluorenylmethyloxycarbonyl (Fmoc). Preferably, the non-protected amino acid is L-proline.

Concerning non-protected amino acids, good amide formation is obtained with L-proline and D-proline. Low amide formation is detected for L-phenylalanine, L-tryptophan, L-alanine, L-methionine and L-leucine. However, for other tested amino acids (L-tyrosine, L-glutamic acid, L-valine, L-histidine, L-glutamine, D-aspartic acid and D,L-serine) no amide formation is observed by HPLC-MS. Surprisingly even racemization free synthesis of L-prolinamide is observed with L-proline as substrate.

Figure 1:
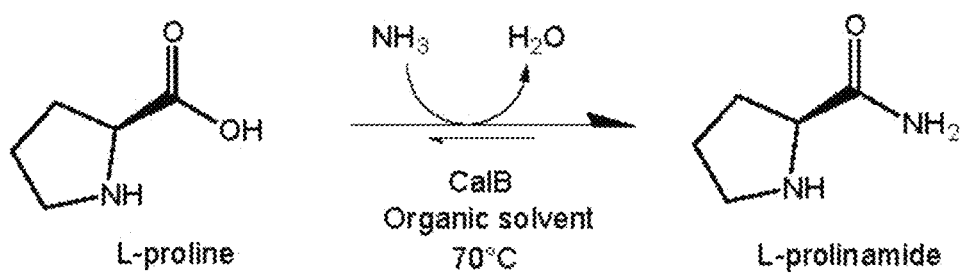
FIG. 1 depicts the reaction scheme of the biocatalytic amidation of L-proline in organic solvent with ammonia forming L-prolinamide and water.

Herein, the biocatalytic amidation of unprotected amino acid, for example L-proline, with ammonia in one step is described (FIG. 1).

Figure 11:
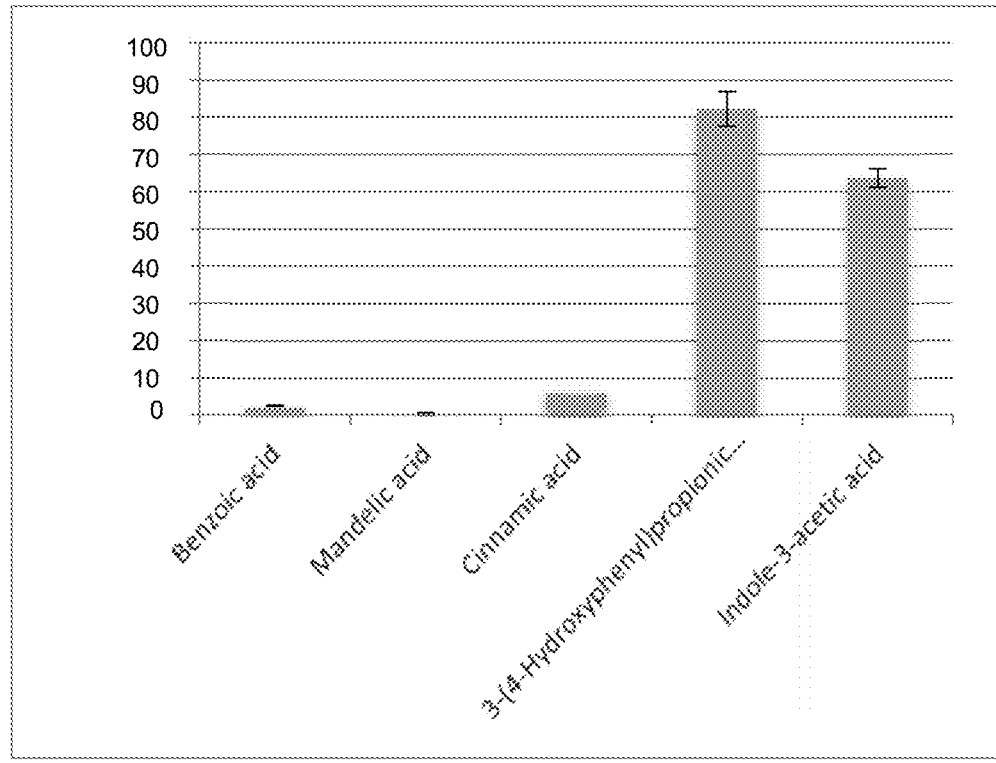
FIG. 11 shows the biocatalytic amidation of various carboxylic acids with $NH_3$.

To investigate the substrate scope of the reaction system, different carboxylic, aromatic and amino acids are tested with 2-methyl-2-butanol (2M2B or MeBuOH) as solvent. Under standard conditions with $NH_3$ and CalB435 indole-3-acetic acid and 3-(4-hydroxyphenyl) propionic acid show significantly higher amide formation than cinnamic acid (FIG. 11). Almost no conversion is observed with benzoic acid or mandelic acid with CalB 435 and $NH_3$.

Different organic solvents are evaluated with highest amide yields in diisopropylether and tert-butyl methyl ether. The right choice of enzyme, ammonia source and solvent appear to determine whether amidation of a substrate takes place. Bulky substrates such as indole-3-acetic acid are converted very well—adding the amino group of L-tryptophan, however, reduces conversion to trace amounts. Adding a hydroxyl group to the aromatic ring as in 3-(4-hydroxyphenyl)propionic acid, on the other hand, results in high conversions above 80%.

When protected amino acids are tested, low conversion to the amide is measured for N-Cbz-L-alanine, whereas no amidation of N-Cbz-L-phenylalanine is detected by HPLC-MS. It turned out, that the choice of solvent is also a fundamental parameter in this respect. Previously, very high conversions of N-Cbz-L-proline with CalB were obtained in 1,4-dioxane. Interestingly, the conversion decreases significantly when 2M2B is used. This effect is seen with CalB435 as well CalBopt (CalB variant T57A/A89T/G226R/R168K) immobilized on resin 8285 (ECR8285, Purolite®).

Further tests with $NH_3$ in 1,4-dioxane are made. Protected amino acids (N-Fmoc-L-proline, N-Cbz-L-alanine), aliphatic acids (hexanoic acid, octanoic acid, decanoic acid), various carboxylic acids with an aromatic moiety (3-phenylpropionic acid, 3-(4-hydroxyphenyl)propionic acid, indole-3-acetic acid, 2-(4-isobutylphenyl) propionic acid (ibuprofen), 2-phenylpropionic acid, 3-hydroxy-4-methoxyphenylacetic acid) and cyclic acids (cyclopentane carboxylic acid, cyclohexane carboxylic acid) are converted to the amide. The results indicate that highest conversions in 1,4-dioxane with $NH_3$ are obtained with long-chain or cyclic aliphatic acids and bulky aromatic acids.

Enzymes for catalyzing the amidation of biomolecules encompass several structural and functional protein families. Amidation may, for example, be achieved via transacylation. Several enzymes catalyze substitution of an acyl acceptor through covalent tethering of the acyl donor. Many enzymes of the serine protease family and α/β hydrolase fold superfamily have been shown to catalyze transacylation.

Two classes of enzymes of interest belong to the α/β hydrolase fold superfamily: the lipases (triacylglycerol hydrolases; E.C. 3.1.1.3) and the esterases (carboxylesterase; E.C. 3.1.1.1). However, lipases prefer long-chain as opposed to short-chain acylglyceride substrates, while esterases tend to use relatively polar substrates (Goswami A., et al., *Mol Biosyst.* 2015 Feb. 20; 11(2): 338-353). Further, also proteases or amidases might be used. Suitable enzymes may be derived for example, from *Candida antarctica, Candida rugosa, Pseudomonas* sp., *Rhizopus arrhizus* and *Rhizomucor miehei* and Subtilisin A.

*Candida antarctica* lipase (CAL) is one of the most thoroughly studied enzymes and converts amines and esters into amides (Yang B. et al., Indian J. Chem. 44B, June 2005, 1312-1316). Improved CALB variants have been reported by Xiang-Quian Peng (Appl Biochem Biotechnol (2013) 169:351-358). The described variants have improved thermostability, e.g., the variant T57A/A89T/G226R/R168K (CalBopt, SEQ ID NO:1).

Enzyme engineering and the use of a thermostabilized CalB variant further increases conversion.

As used herein, the term "variant" refers to enzymes obtained by alteration of a precursor amino acid sequence and/or structure thereof. A variant may be a substitution, deletion or addition variant of the amino acid sequences of the enzyme. However, the modifications in a variant sequence should not alter the functional properties of the enzyme. Thermostable variants of CalB are for example described by Xiang-Qian Peng (2013).

In one embodiment of the invention, the robust and inexpensive lipase *Candida antarctica* B (CalB) is employed in immobilized form in purely organic solvent with water being the only by-product formed. In contrast to the tedious chemical amidation process involving thionyl chloride and racemization issues, L-prolinamide is formed in one step in an enantiomerically pure form. The improved process is applicable at large scale and represents a promising alternative for industrial production of L-prolinamide, a valuable pharmaceutical building block for e.g., antidiabetic drugs.

For efficient amide formation in pure organic solvent, the enzyme has to be stabilized, e.g., by immobilization. Through immobilization, the enzymes are not only stabilized but can also be reused. After use, the enzymes are easy to remove from the reaction mixture. In this way, they can be used under a variety of processing conditions. Desirably, the substrate and reaction specificity and enzyme reactivity should not be lost as a result of immobilization.

The enzyme is immobilized to a suitable particulate support or matrix. The immobilized enzyme as described herein refers to an enzyme that is physically attached to a solid support by adsorption or chemically attached to a solid support by ionic or covalent bonds.

With regard to the immobilized enzyme described herein the solid support is a resin. Resins can be made from any suitable composition including, but not limited to, polyacrylate, polymethacrylate, polystyrene, silica, and styrene/DVB copolymer. Such resins can include functional groups and facilitate adsorption, covalent bonding or ionic bonding of the enzyme to the resin. Suitable functional groups include, but are not limited to, epoxide, ester, alkyl aromatic groups, hydroxyl, carboxylic groups, and quaternary ammonium groups. Additionally, other structural features such as octadecyl and resins that include a porous structure facilitate adsorption of the enzyme.

A comparison of different preparations of CalB shows that improved results are obtained with CalB435 from Novozymes and CalB expressed in *P. pastoris* and immobilized on resin ECR8806 Purolite® (CalB 8806). In both cases, immobilization occurs via adsorption. CalB 435 from Novozymes is adsorbed on macroporous Lewatit VP OC 1600, consisting of poly(metacrylic acid) with divinylbenzene for cross-linking. Numerous applications of this preparation are reported, often due to its exceptional activity and stability. Nevertheless, recycling of CalB435 can be problematic due to enzyme leaching and mechanical instability. The octadecyl substituted methacrylate resin of ECR8806 Purolite® allows reversible but at the same time very strong adsorption. In contrast to covalent binding, adsorption causes almost no conformational change, which may explain higher conversions by the latter. When CalB is immobilized on resin ECR8285 from Purolite® (CalB 8285), covalent binding between the amine groups of the enzyme and the epoxy groups of the epoxy/butyl methacrylate carrier takes place.

Figure 9:
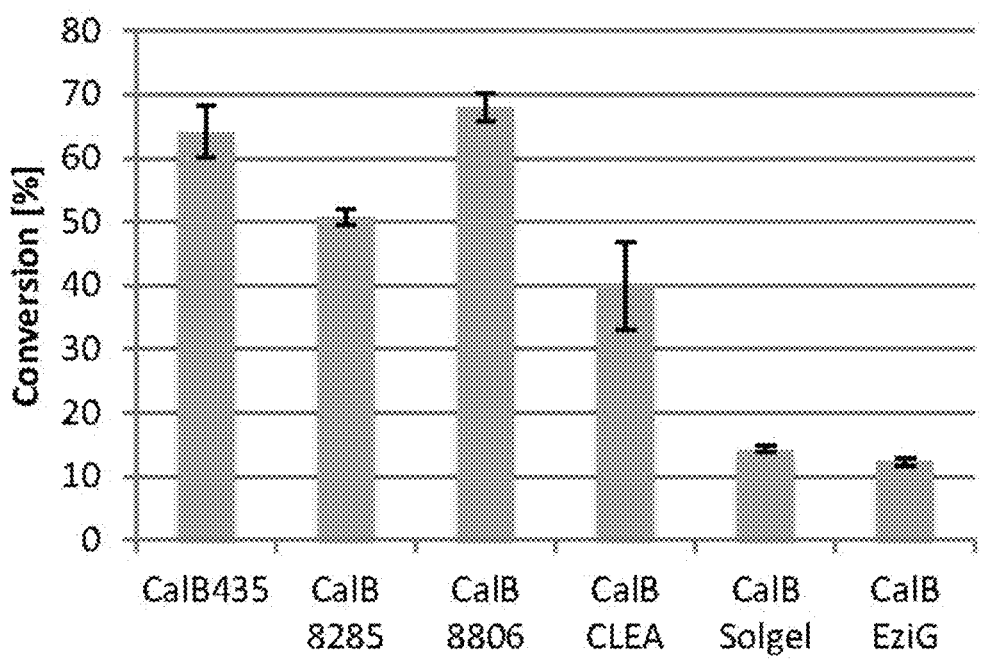
FIG. 9 shows the effect of different CalB preparations normalized to the same amount of enzyme preparation.
Figure 10:
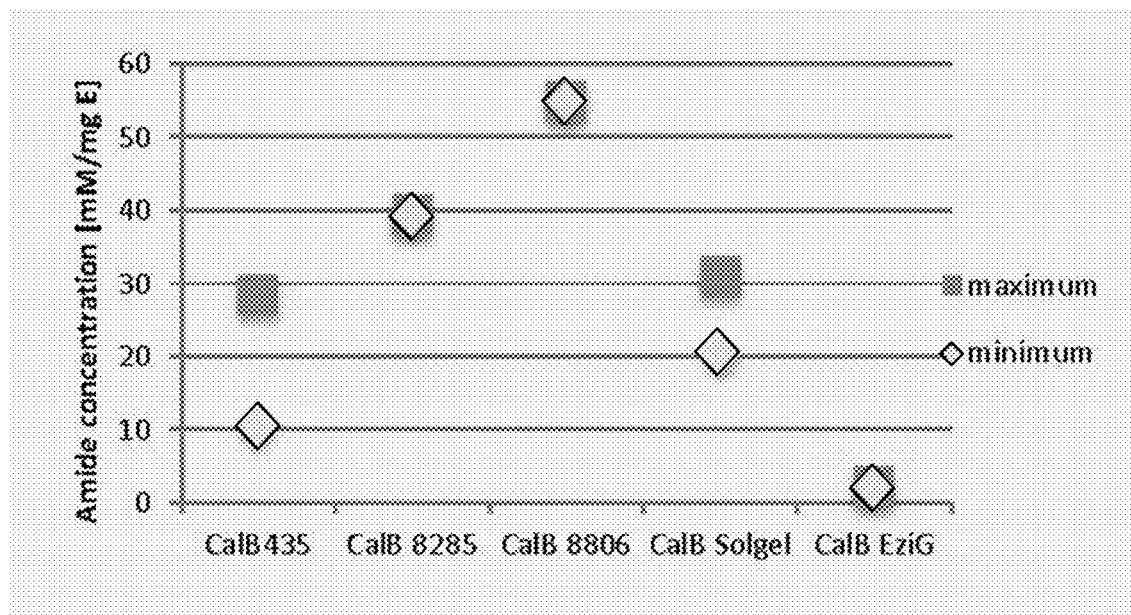
FIG. 10 shows the effect of different CalB preparations normalized to the enzyme loading (in amide concentration per mg CalB).

Furthermore, cross-linked enzyme aggregates (CLEAs) 32,33, sol-gel entrapped CalB34 and EziG™, immobilized on controlled porosity glass, are tested. The transformation of L-proline (33 mM) with $NH_3$ in 2M2B (0.5 M, 500 µL) is carried out as described herein with various CalB preparations (8.3 mg) for 16 h at 700 rpm and 70° C.; addition of MeOH and HPLC-MS analysis. In FIG. 9 a comparison with the same amount of enzyme preparation, is shown. CalB 8806 lead to highest amide formation. For ECR8806 Purolite® and ECR8285 Purolite® the same amount of CalB (5 mg) is immobilized on the resins (100 mg). In the case of EziG, 100 mg of the preparation contain 15.3 mg of CalB. According to literature, the enzyme loading on the support of CalB 435 varies between 8.5 and 20 w/w %. For the sol-gel preparation (300 mg), c-LEcta CalB powder (50 mg, containing 10-15% enzyme) is used. For the CalB CLEAs from Sigma-Aldrich, the activity (2.6 U/mg) is known, but not the protein loading. The varying enzyme loadings make a comparison difficult. When amide formation is normalized to the actual amount of enzyme, highest product concentrations are again received with the preparation CalB 8806 and the improvement over CalB435 is more pronounced (FIG. 10). The transformation of L-proline (33 mM) in $NH_3$ and 2M2B (0.5 M, 500 µL) is carried out as described herein with various CalB preparations (8.3 mg) for 16 h at 700 rpm and 70° C.; addition of MeOH and HPLC-MS analysis.

The choice of solvent turns out to be a crucial parameter, influencing the solubility of substrate, product and ammonia, the water activity and enzyme stability. The solubility of L-proline is highest in water (1500 g/L at 20° C.), followed by methanol (17.5 w % at 20° C.) and short chain alcohols. However, water causes the reverse hydrolysis reaction and hinders amidation due to the large excess of water as nucleophile in comparison to ammonia. Amidation activity in methanol is very low, which might to be due to inhibition effects. The substrate solubility of L-proline in primary alcohols such as n-butanol (3.1 w % at 20° C.) is significantly higher than in iso-butanol (0.4 w % at 20° C.), a secondary alcohol, or 2-methyl-2-butanol (2M2B, 0.02 w % at 20° C.), a tertiary alcohol. Although this might suggest highest amide formation in primary alcohols, surprisingly best results are obtained in tertiary alcohols.

Figure 2:
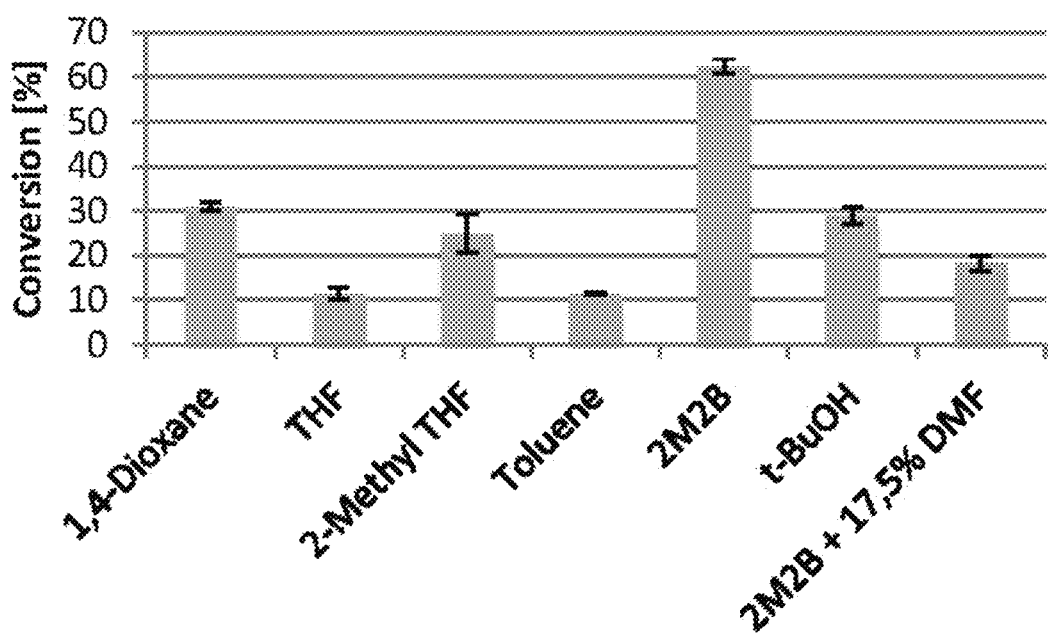
FIG. 2 depicts transformation of L-proline (33 mM) performed with CalB435 in different solvents with ~0.5 M $NH_3$ (500 μL).

Numerous organic solvents are tested for amidation of L-proline (FIG. 2). Previous experiments with N-Cbz-L-proline suggest using toluene or t-BuOH/DMF (Nuijens (2012)). Despite the low solubility of L-proline in 2M2B, highest conversions are obtained in this solvent. It has to be noted, that the solubility increases upon addition of $NH_3$ or the product, L-prolinamide. In contrast to primary alcohols, no ester formation is observed with the tertiary alcohol. All other solvents, including 1,4-dioxane, tetrahydrofuran (THF), 2-methyl-THF, toluene, t-BuOH and addition of DMF as co-solvent to 2M2B show conversions around 10-30%. Using 2M2B as solvent doubles the conversion to around 60%.

Alcohols are ranked as one of the 'greenest' solvent classes in solvent selection guides, clearly superior to hydrocarbons, ethers or halogenated solvents. Therefore, 2M2B is not only desirable based on the high conversions obtained but also because of environmental aspects concerning its sustainability.

Figure 4A:
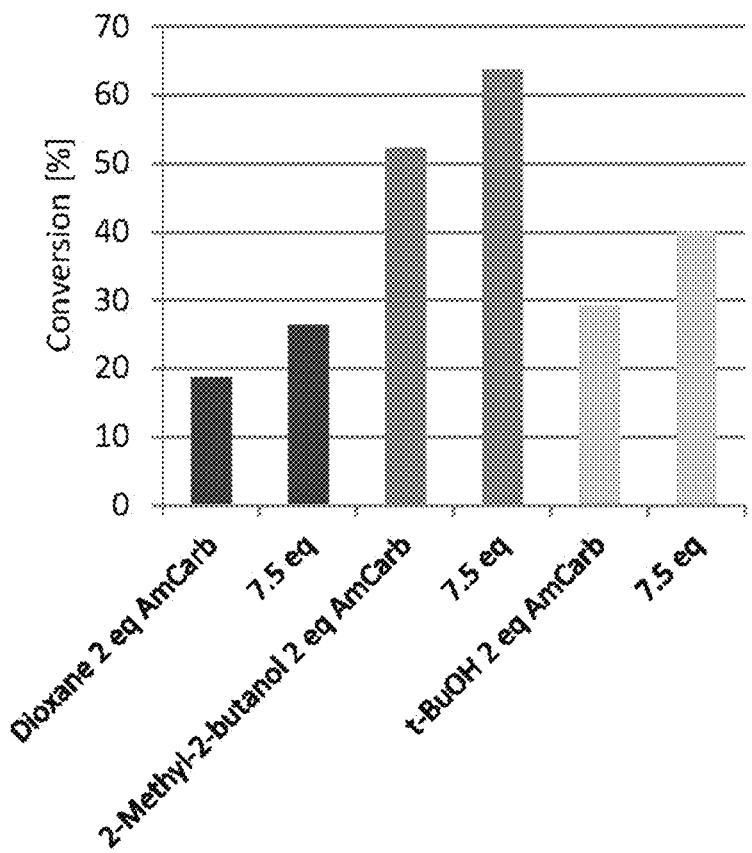
FIG. 4 shows the transformation of L-proline in different solvents with ammonium carbamate and CalB 435. Conversions and concentrations of substrate and product in [mM] are shown.
Figure 4B:
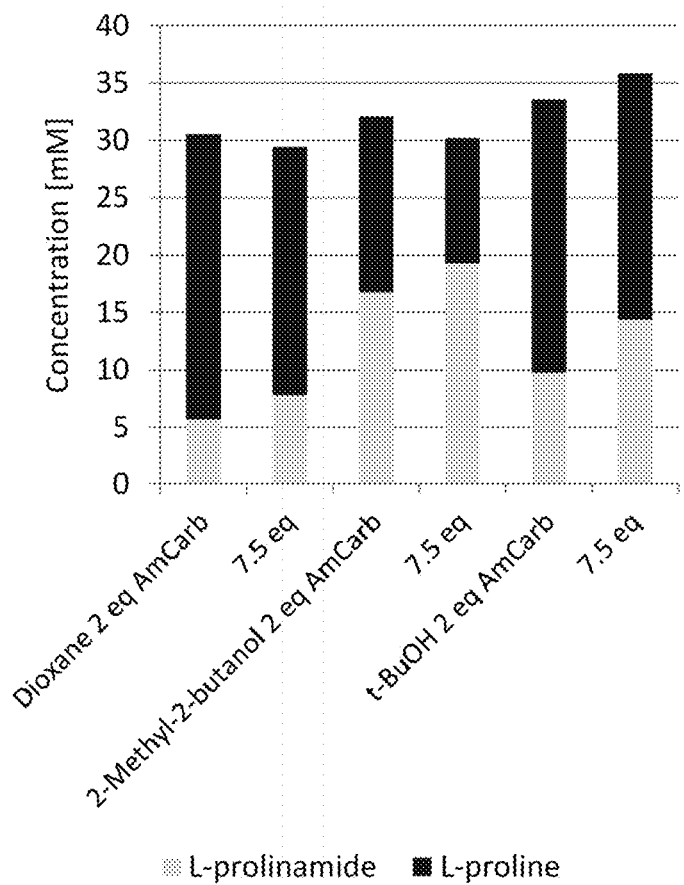

Tests with tertiary alcohols, 2-methyl-2-butanol and t-butanol, and ammonium carbamate as ammonium source are made. Further tertiary alcohols do not seem to be suitable at large scale due to their high prices. With increased amounts of ammonium carbamate (2 eq and 7.5 eq), the amide formation is increased. Best results are obtained in 2-methyl-2-butanol, followed by t-BuOH and 1,4-dioxane (FIG. 4A, 4B).

Alternatively, also liquid salts may be employed in the method of the present invention. Liquid salts also known as "ionic liquids" are generally organic salts with melting points below 100° C. and often below room temperature. Liquid salts may include those derived from ammonium halides and Lewis acids, such as $AlCl_3$, $TiCl_4$, $SnCl_4$, and $FeCl_3$.

A further important aspect of the invention is the ammonia source. Suitable sources are for example, ammonia ($NH_3$), ammonium carbamate, ammonium carbonate, benzylamine, ethanolamine, hexylamine, 2-phenylethylamine, or 3-phenylpropylamine, or any mixtures thereof.

Litjens et al. (1999) compared the synthesis of amides from carboxylic acids with ammonium bicarbonate, ammonium carbamate and gaseous ammonia for the synthesis of butyramide and oleamide. The authors noticed a decrease in the reaction rate with increasing ammonia concentrations and concluded that an appropriate ratio of acid and ammonia concentrations is required to avoid precipitation of the ammonium salt. This was achieved by gradual addition of slowly dissolving ammonium carbamate.

Figure 12A:
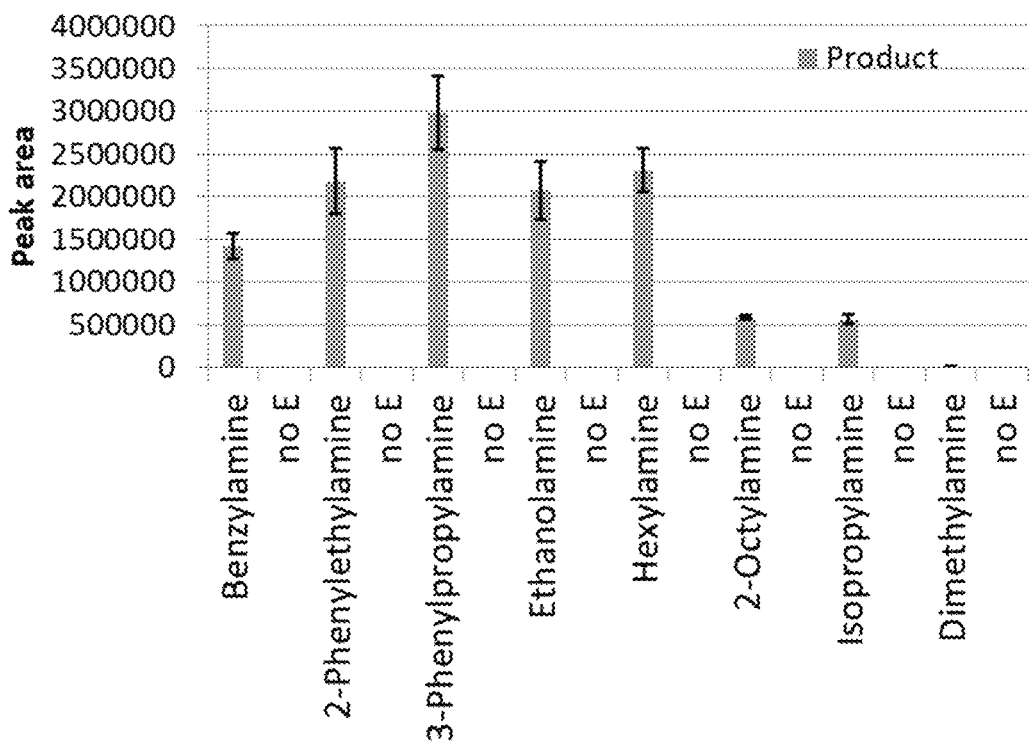
FIG. 12 shows the amine donor scope.
Figure 12B:
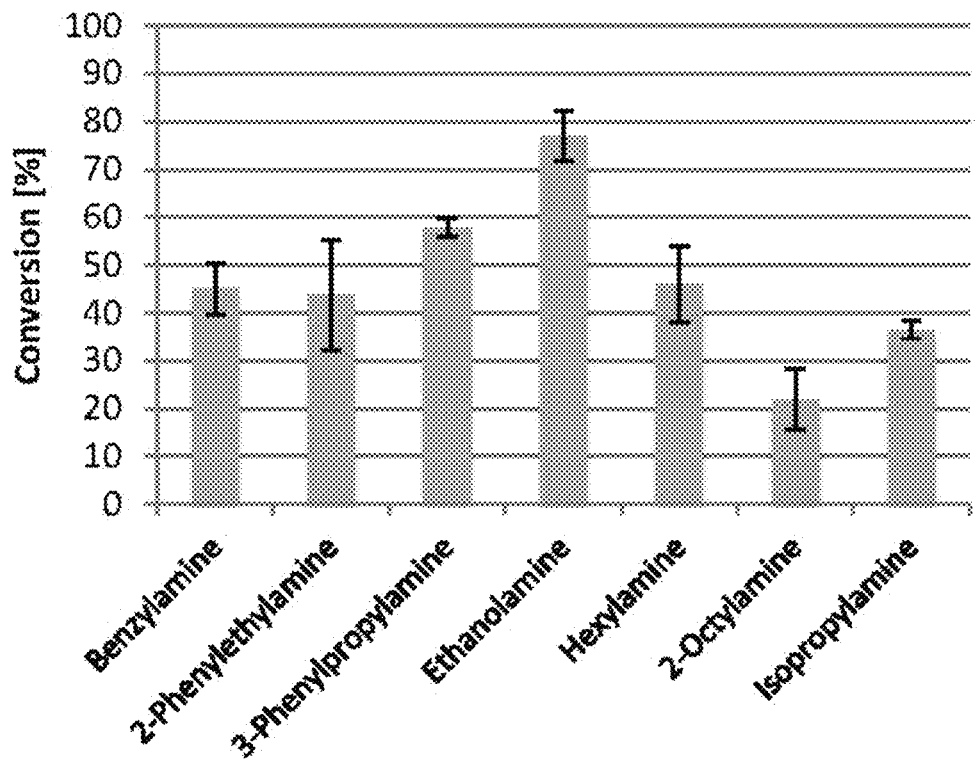

Amidation of L-proline can be performed with $NH_3$ or ammonium salts (e.g. ammonium carbamate, or ammonium carbonate, tested in 1,4-dioxane). N-substituted amides of L-proline can be produced by using different alkylamines as amine donor, e.g. benzylamine, ethanolamine, hexylamine, 2-phenylethylamine, 3-phenylpropylamine. Amidation of L-proline (20 mM) with different alkylamines (5 eq) in 2M2B (500 µL) with CalB435 (10 mg) is performed at 70° C. with 700 rpm for 16 h, dissolved in MeOH and analyzed by HPLC-MS (FIG. 12). However, no significant amide formation was observed with dimethylamine. Conversions with aromatic amines and short aliphatic amines (ethanolamine, hexylamine) were higher than with 2-octylamine or isopropylamine.

Figure 5:
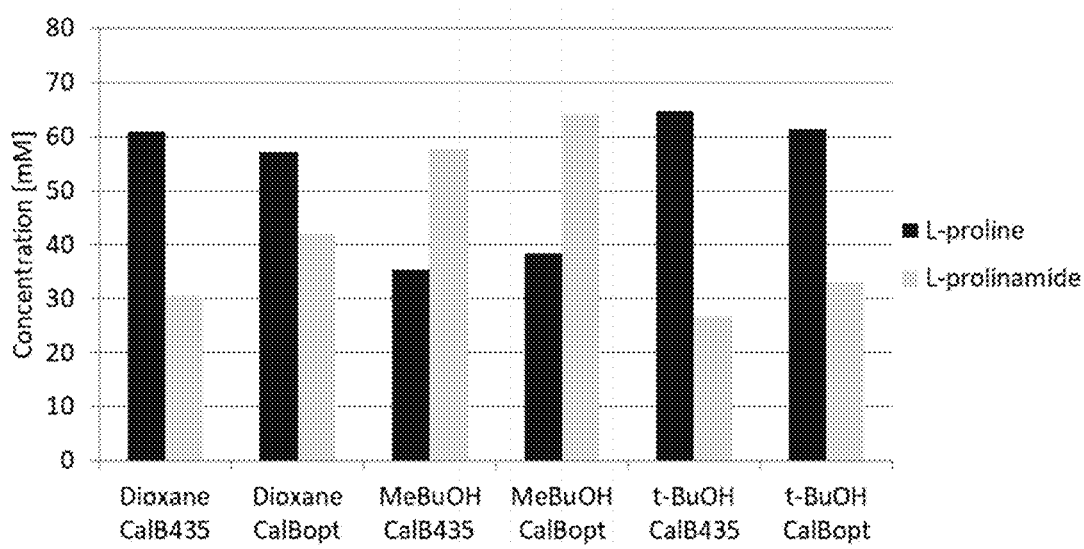
FIG. 5 shows the results of the biocatalytic transformation of L-proline in $NH_3$, 1,4-dioxane (500 μL) or 2-methyl-2-butanol (MeBuOH) or t-butanol (t-BuOH).
Figure 6:
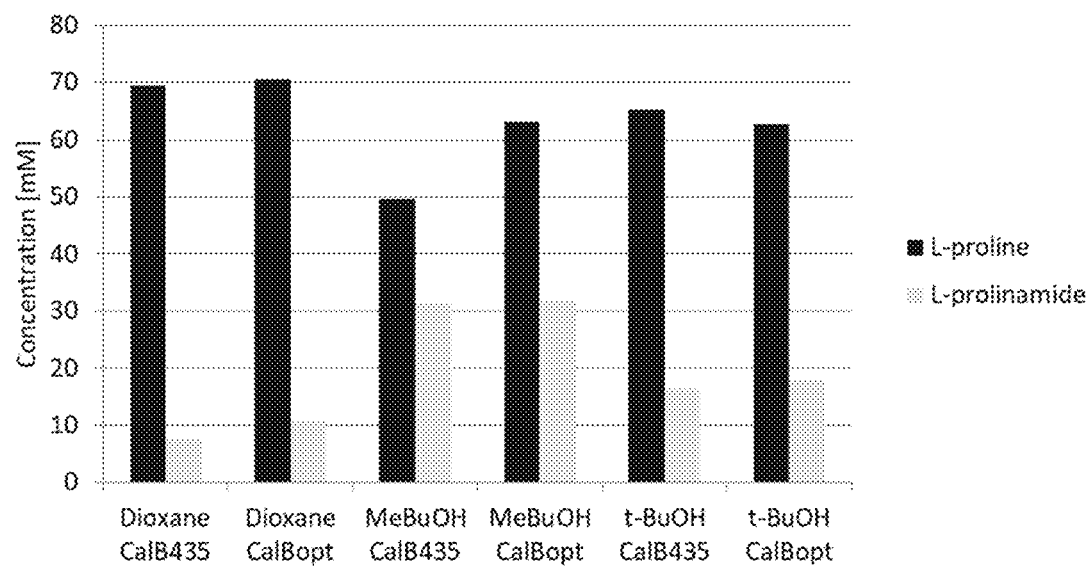
FIG. 6 shows the results of the biocatalytic transformation of L-proline with addition of ammonium carbamate (30 mg, 7.5 eq).

Experiments with $NH_3$ confirm that 2-methyl-2-butanol is the solvent of choice (FIG. 5). The reactions are performed as described herein with CalB 435 (8.3 mg) for 88 h at 700 rpm and 70° C.; addition of MeOH and HPLC-MS analysis. Slightly higher amounts of product are formed with CalBopt (for example, produced by fermentation, immobilization and lyophilization according to Vogl et al. (2016)) compared to CalB435 (from Novozymes). When ammonium carbamate (7.5 eq) is used as ammonium donor, the product formation is significantly lowered for all solvents (FIG. 6). The reaction is carried out as described herein with L-proline (5.8 mg, 100 mM) in 1,4-dioxane, 2-methyl-2-butanol (Me-BuOH) or t-butanol (500 µL) with addition of ammonium carbamate (30 mg, 7.5 eq). The reactions are performed with CalB 435 (8.3 mg) for 88 h at 700 rpm and 70° C.; addition of MeOH and HPLC-MS analysis One embodiment of the invention relates to the method as described herein, wherein the ammonia source is ammonia ($NH_3$), ammonium carbamate, ammonium carbonate, ammonium formate, ammonium benzoate, benzylamine, ethanolamine, hexylamine, 2-phenylethylamine, or 3-phenylpropylamine, or any mixtures thereof, preferably ammonia.

In one embodiment of the invention the ammonia is comprised in the organic solvent. Ammonia may be dissolved, admixed or partitioned in the organic solvent or may be present as gaseous bubbles.

Figure 7:
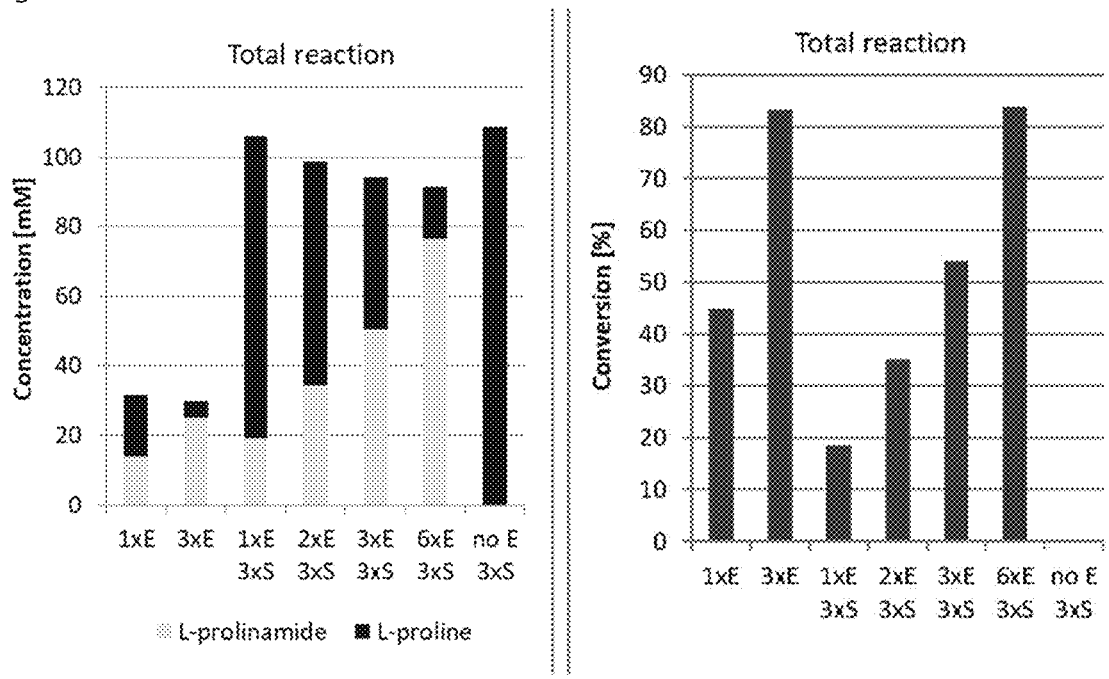
FIG. 7 shows the results of the biocatalytic transformation of L-proline in 2-methyl-2-butanol, $NH_3$, CalB 435 or the 2-, 3-, 6-fold amount of enzyme (E, i.e. CalB435) and substrate (S, i.e. L-proline).

When the enzyme loading is increased, amide formation increases as well (FIG. 7). The reaction is carried out as described herein with L-proline as substrate (1.9 mg, 33 mM or threefold concentration of substrate (3×S), 5.7 mg, 100 mM) in 2-methyl-2-butanol with about 0.5 M $NH_3$ (500 µL). The reactions are performed with CalB 435 as enzyme (8.3 mg or the 2-, 3-, 6-fold amount of enzyme (E)) for 16 h at 700 rpm and 70° C.; addition of MeOH and HPLC-MS analysis of the reactions. No amide formation is obtained without enzyme. Increasing the substrate loading three-fold from 33 mM to 100 mM do not impair amide formation. In FIG. 7, the total reaction mixture is analyzed after fully dissolving substrate and product by methanol addition.

Figure 8:
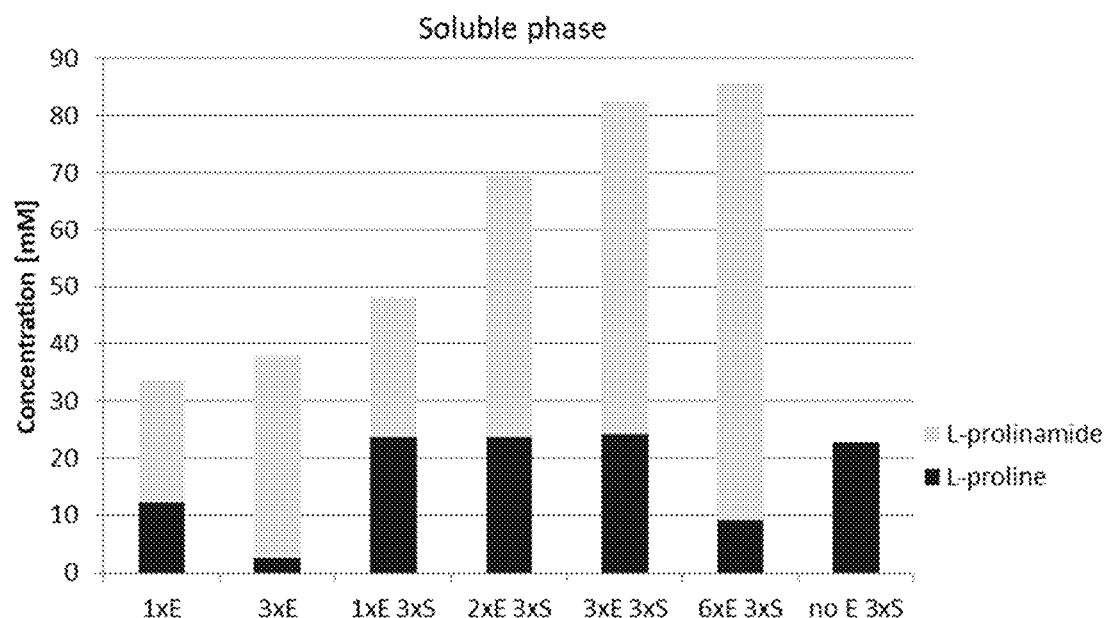
FIG. 8 shows the result of the biocatalytic transformation of L-proline or of the triple amount thereof in 2-methyl-2-butanol and $NH_3$.

In contrast to that, in FIG. 8 the soluble phase of the reaction is analyzed at room temperature. The reaction is carried out as described herein with L-proline (1.9 mg, 33 mM or threefold concentration of substrate (3×S), 5.7 mg, 100 mM) in 2-methyl-2-butanol with about 0.5 M $NH_3$ (500 µL). The reactions are performed with CalB 435 (8.3 mg or the 2-, 3-, 6-fold amount of enzyme (E)) for 16 h at 700 rpm and 70° C.; HPLC-MS analysis of the soluble phase of the reaction. As expected, the amide concentrations are in both cases similar. The dissolved concentration of L-proline, however, is about 23 mM. The solubility limit is probably mainly depending on the current $NH_3$ concentration and temperature. In the reaction with six-fold enzyme and three-fold substrate (100 mM), the dissolved L-proline concentration is noticeably lower (about 10 mM), although the same concentration was expected.

Figure 3:
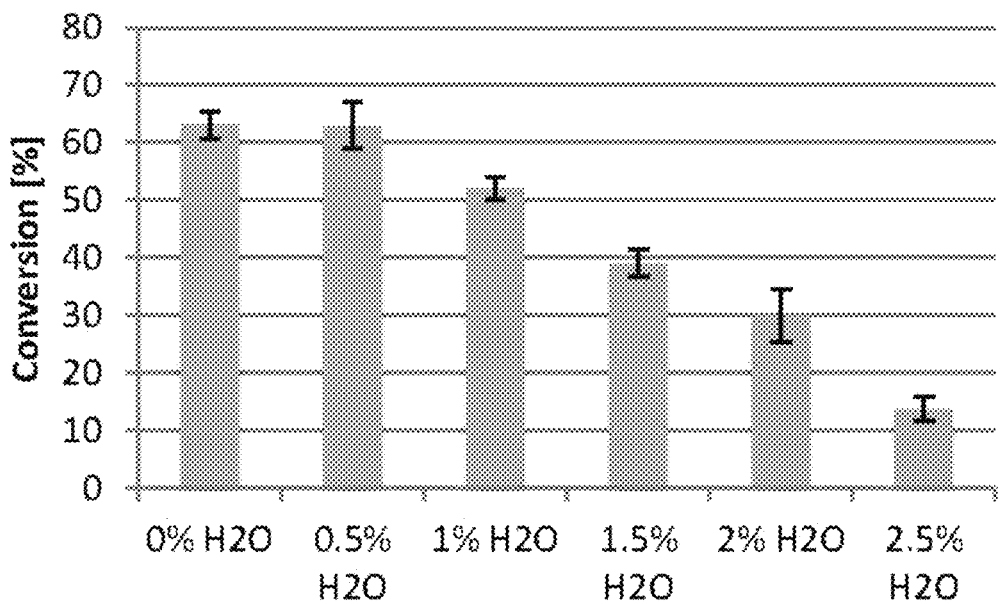
FIG. 3 shows the effect of adding $H_2O$ to the reaction of L-proline (33 mM) in 2-methyl-2-butanol (MeBuOH) with ~0.5 M $NH_3$ (500 μL) performed with CalB435.

Previous publications describe that even trace quantities of water in the organic solvent might cause hydrolysis of the acyl donor. The effect of adding different water concentrations (0.5-2.5 v/v %) to 2M2B is investigated to gain insight into the amount of water tolerated by the reaction system. The water content in the solvent before reaction is <0.10%. For efficient amidation, low water concentrations (preferably <0.5 v/v %) in reaction media are preferred (FIG. 3). A decrease in amide formation is seen when the water concentration is increased, but the reaction is still observable, despite some additional water (e.g., 2 v/v % water reduced the conversion by half). These results are especially important for long-term production at larger scale, to get data on how much water needs to be removed from the media in case of solvent recycling.

According to a further embodiment of the invention the method is carried out in a reaction medium, wherein the reaction medium comprises less than 2 v/v %, 1.5 v/v %, 1.0 v/v %, 0.75 v/v %, or less than 0.5 v/v % water.

An industrial biocatalytic process according to the invention using a chemically defined medium can be performed as a batch, a repeated batch, a fed-batch, a repeated fed-batch or a continuous reaction process.

Most biocatalytic methods for transformation of compounds are carried out in in a liquid medium. In practice, such transformation processes are carried out in liquid media and are performed as a batch process. The batch process is a discontinuous process, where all medium components are added directly, as a whole, to the medium before the start of the transformation process. In a repeated batch process, a partial harvest of the transformed compound accompanied by a partial supplementation of complete medium occurs, optionally repeated several times.

In a fed-batch process, either none or part of the compounds comprising one or more of the structural and/or catalytic elements is added to the medium before the start of the reaction and either all or the remaining part, irrespectively, of the components comprising one or more of the structural and/or catalytic elements is fed during the reaction process. The components which are selected for feeding can be fed to the reaction process jointly or separately from each other.

In a repeated fed-batch or a continuous reaction process, the complete start medium is additionally fed during the reaction process. The start medium can be fed jointly or separately from the structural element feed(s). In a continuous process, the removal of part of the reaction medium and the target compound occurs continuously. The reaction process is thereby continuously replenished with a portion of fresh medium corresponding to the amount of withdrawn reaction medium.

The method according to the invention may be a "laboratory-scale" process in bioreactors or the like in the range of 500 mL to 10 L, shake flasks or the like in the range of 10 to 1000 mL, in cuvettes, glass vials, falcon tubes or the like in the range of 1 to 100 mL, in microtiter plates, or the like in the range of 5 µL to 1 mL.

However, the method according to the invention may be a "large-scale" process in reaction vessels from 10 L up to 200 m$^3$, or 100 L to 100 m$^3$.

EXAMPLES

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

Example 1—Transformation of L-proline

Standard Reactions with L-Proline in Batch at Small Scale
For the biotransformation under standard conditions L-proline (1.9 mg, 33 mM) and immobilized CalB (8.3 mg), CalB435 from Novozymes or immobilized CalB variants, were used (unless otherwise stated). The reactions were performed in about 0.5 M NH$_3$ in organic solvent (2-methyl-2-butanol, 1,4-dioxane or t-BuOH, 500 µL) in small glass vials sealed with a cap and a septum and shaken for 16 h at 700 rpm and 70° C. in an Eppendorf Thermoshaker Comfort.

After the reactions, MeOH (500 µL) was added to fully dissolve substrate and product. The samples were diluted to 1 mM substrate concentration (1:33) with MeOH. As internal standard D,L-norvaline (0.5 mM) was added and the samples were vortexed, centrifuged (13,000 rpm, 2 min), filtrated through cotton wool and analyzed by HPLC-MS.
Reactions with L-Proline in HEL Pressure Reactor
For the biotransformation under pressure the HEL Digi-CAT reactor system, which tolerates reaction conditions up to 200 bar and 300° C., was used. L-proline (167 mg, 145 mM) and CalB (167 mg, CalB435 from Novozymes or immobilized CalBopt) were filled in the reactor. The reactions were performed with 2-methyl-2-butanol or 1,4-dioxane as solvent (10 mL) at 70° C. A volume of 10 mL was used to ensure that the ammonia gas is bubbling through the reaction mixture. A stirring speed of 150 rpm with a cross-shaped stir bar was used to avoid grinding of the enzyme beads. The reactor was closed tightly and NH$_3$ gas was applied with a pressure of 0.6-1.4 bar. The reactions were run for 6 h at 70° C. After the biotransformation, a sample of the reaction solvent was taken and filtered to analyze the soluble concentrations of substrate and product. The samples were diluted (1:80) with MeOH+0.1% formic acid. As internal standard D,L-norvaline (0.5 mM) was added and the samples were analyzed by HPLC-MS.
Analytics of L-Proline
For HPLC-MS analysis an Agilent 1200 Infinity system was equipped with a Zorbax 300-SCX 4.6×250 mm 5 Micron column from Agilent. Analysis was done by isocratic elution using 90% H$_2$O+0.1% formic acid and 10% MeOH+0.1% formic acid for about 20 min. The flow rate was set to 1 mL/min and the maximal pressure limit to 400 bar. Analysis was performed in positive SCAN (114.5-300 m/z) and SIM modes (115 m/z for L-prolinamide, 116 m/z for L-proline, 118 m/z for D,L-norvaline as internal standard). A sample volume of 2 µL was injected.

L-proline and L-prolinamide calibration curves were made with reference solutions from 0.03-4 mM in MeOH containing D,L-norvaline (0.5 mM) as internal standards.

Standard procedure for sample preparation: the reactions were dissolved in MeOH containing 0.5 mM D,L-norvaline as internal standard (500 µL). The samples were diluted to 1 mM in MeOH with 0.5 mM D,L-norvaline, vortexed, centrifuged (13,000 rpm, 2 min) and filtered through cotton wool before they were measured by HPLC-MS.

Example 2—Transformation of Cbz-L-proline

Biocatalytic Amide Formation from Cbz-Proline
For the biotransformation under standard conditions Cbz-L-proline (4.1 mg, 33 mM) and immobilized CalB (8.3 mg, Novozyme 435 or own immobilized CalB variants) were used with 0.5 M NH3 in 1,4-dioxane (500 µL). The reactions were performed at 70° C. and 700 rpm for 16 h (unless otherwise stated) in an Eppendorf Thermoshaker Comfort.

The reaction solution was then diluted to 1 mM in MeOH with L-phenylalanine (3 mM) as internal standard, vortexed, centrifuged (13,000 rpm, 2 min) and filtered through cotton wool prior to analysis by HPLC-MS.
Analytics for Cbz-L-Proline
For HPLC-MS analysis an Agilent 1200 Infinity system was equipped with a Poroshell 120 EC-C18 4.6×50 mm 2.7 Micron column from Agilent. Analysis was done with a gradient of water/acetonitrile+0.1% formic acid (0 min: 100% water+0.1% formic acid, 5 min: 100% acetonitrile+0.1% formic acid, 8 min: 100% water+0.1% formic acid). The flow rate was set to 0.75 mL/min and the maximal pressure limit to 600 bar. Analysis was performed in positive SCAN (115-350 m/z) and SIM modes (249 m/z for Cbz-prolinamide, 250 m/z for Cbz-proline, 166 m/z for L-phenylalanine as internal standard). A sample volume of 1 µL was injected.

For preparation of the calibration curves reference solutions with a concentration of 0.1 mM-4 mM of Cbz-proline and Cbz-prolinamide, respectively, were made in MeOH. L-phenylalanine (3 mM) was used as internal standard and added to each sample.

Standard procedure for sample preparation: the reaction solvent was diluted to 1 mM in MeOH with L-phenylalanine (3 mM) as internal standard, the samples were vortexed, centrifuged and filtered through cotton wool before they were measure by HPLC-MS.

Example 3—Reactions with New Substrates

Testing Different Acids with CalB 435 and $NH_3$

Different acids (33 mM) were incubated with CalB 435 (8.3 mg) in 0.5 M $NH_3$ in 1,4-dioxane (500 µL). A reaction sample plus a reference sample without the enzyme was prepared and incubated for each substrate. After 16 h reaction time at 70° C., the samples were diluted and analyzed. Product formation was confirmed by HPLC-MS (using the method described in above for Cbz-proline) before the reactions were analyzed by GC-MS or HPLC-UV. GC-MS: The samples were diluted and unconverted substrate was derivatized to the corresponding methyl esters. The derivatization procedure was performed by the addition of MeOH (60 µL) to the sample (150 µL) and subsequent addition of a 2 M solution of trimethylsilyldiazomethane in hexanes (10 µL). After 10 min incubation at room temperature, the samples were measured with GC-MS. The ratios of substrate and product peak areas were compared. An Agilent 7890A GC-system was used, equipped with an Agilent 5975C mass selective detector (EI 70 eV) and an HP-5 MS column (30 m×0.25 mm×0.25 µm) using helium as carrier gas (flow=0.5 mL/min).

HPLC-UV measurements at 210 nm were used for analysis of the following substrates: 3-phenylpropionic acid, ibuprofen, 3-hydroxy-4-methoxy-phenylacetic acid and 3-phenylpropionic acid.

Analytics for Alternative Substrates

HPLC-UV experiments were performed on an HPLC Agilent 1260 Infinity system with a diode array detector and a reversed phase Phenomenex Luna column C18 (100 Å, 250×4.6 mm, 5 µm, column temperature 24° C.). All compounds were spectrophotometrically detected at 210, 220, 254, 263, 280 and 310 nm, respectively. A flow rate of 1 mL/min was set and a maximum pressure of 250 bar. An injection volume of 5 µL was used. The method was run over 22 min with a gradient of $H_2O$/trifluoroacetic acid (TFA, 0.1%) and ACN/TFA (0.1%) as the mobile phase (0-2 min 5% ACN/TFA, 2-15 min 5-100% ACN/TFA, 15-17 min 100% ACN/TFA, 17-22 min 100-5% ACN/TFA).

Standard procedure for sample preparation: addition of ACN/H2O 1/1+3% TFA (or MeOH, 500 µL) to the reaction to dissolve substrate and product and dilution with ACN/$H_2O$ 1/1+3% TFA (in total 1:8 diluted). The samples were vortexed, centrifuged (13,000 rpm, 2 min), filtered through cotton wool and analyzed by HPLC-UV measurements.

Example 4—Additional Methods $NH_3$ Quantification

The $NH_3$ concentration in 2-methyl-2-butanol was determined after bubbling $NH_3$ through the solvent (60 mL) in an open round bottom flask while stirring with a magnetic stir bar for ~2 h. The Ammonia Assay Kit from Sigma-Aldrich (MAK310) was used according to the manual of the supplier. First, the frozen reagents were allowed to come to room temperature. $NH_4Cl$ standards with concentrations of 0 (blank), 0.25, 0.5 and 1 mM $NH_4Cl$ were prepared in $dH_2O$. The samples were diluted with $dH_2O$ (1:600) to obtain concentrations in the linear range of the kit of 0.012-1 mM. Transparent 96-well microtiter plates (MTPs) were used for the measurements in the plate reader. A working reagent mix was prepared, containing Ammonia Assay Buffer (90 µL), Reagent A (4 µL) and Reagent B (4 µL). The standards (10 µL) and samples (10 µL) were pipetted in the MTP before addition of 90 µL working reagent mix and immediate tapping and shaking of the plate in the plate reader. The plate was incubated in the dark at room temperature for 15 min and the fluorescence intensity was measured ($\lambda$ex=360 nm, $\lambda$em=450 nm).

Example 5—Enzyme Engineering

Making Variants of CalB

The rational variants of CalB were generated based on the two-step site-directed mutagenesis protocol (Wang and Malcolm, 1999, 2002) using Q5® High-Fidelity DNA Polymerase (New England Biolabs GmbH). For expression of CalB the $P_{CAT1}$ promoter was used (Vogl et al., ACS Synthetic Biology, 5(2), pp. 172-186 (2016)). The first step of the workflow was the insertion of the desired mutation(s) into the CalB wild type gene by PCR. After transformation into E. coli Top10 F' cells and sequencing, the DNA was transformed into P. pastoris by integration into the genome according to standard protocols (FIG. 13, CalBopt (T57A/A89T/G226R/R168K) protein sequence).

CalB Expression in Pichia pastoris

Colonies of a Pichia pastoris (Komagataella phaffii) strain harboring chromosomal integrated CalB were used to inoculate BMG1% or BMD1% media (450 mL) in a 2.5 L Ultra Yield Flask (UYF). The flasks were incubated at 28° C. and 100 rpm for 60 h. Methanol was added daily to induce and maintain expression of CalB. First BMM5% (50 mL, BMM10) was added followed by additions of pure MeOH (5 mL) every 12 h. After 72 h of protein expression, the cultures were harvested by centrifugation in 500 mL tubes at 5,000 rpm and 4° C. for 15 minutes. The supernatant was transferred in clean bottles and filtered through a membrane with a minimum pore size diameter of 0.45 µm by vacuum filtration.

Media preparation: The following stock solutions were prepared: 500×B: 0.02% D-Biotin, filter sterilized; 10×YNB: 134 g/L Difco™ Yeast Nitrogen Base w/o Amino Acids, 10×D (20%): 220 g/L α-D(+)-Glucose monohydrate, 10×G (20%): 200 g 100% glycerol+800 mL $dH_2O$; 10× PPB (1 M PPB, pH 6.0): 30.13 g/L $K_2HPO_4$*3 $H_2O$, 118.13 g/L $KH_2PO_4$. For preparation of BMD1%/BMG1%/BMM10 (5%) 10×YNB (100 mL/L), 10×PPB (200 mL/L), 10×D/10×G/100% MeOH (50 mL/L) and 500×B (2 mL/L) were added to dH2O after autoclaving. Fermentation of P. pastoris mutS was performed in Sartorius biostat CT/Cplus bioreactors following a methanol dependent protein expression protocol.

Due to the relatively low concentrations of CalB in the supernatant (~0.15 g/L; determined by Bradford protein quantification assay), it had to be concentrated for further immobilization. Cross flow filtration with a 10,000 MWCO filter cassette was performed for larger amounts of samples, whereas Sartorius Vivaspin® 20 tubes with 10,000 MWCO were used when numerous samples with smaller volumes had to be concentrated in parallel (300 mL supernatant were concentrated to 2-5 mL).

Immobilization and Lyophilization of CalB

PD10 desalting columns: PD10 desalting columns from GE Healthcare Life Sciences were used for buffer exchange at small scale according to the recommendations of the supplier. After washing the columns with ddH2O and target buffer (according to Table 2), the sample (2.5 mL) was loaded onto the column. Target buffer (3.5 mL) was then applied to elute the protein and the fraction was collected. Depending on the total sample volume, the last two steps were repeated when required. At the end, the column was washed with $ddH_2O$ and stored in 20% EtOH. The obtained protein solutions were concentrated by centrifugation using Vivaspin 20, 10,000 MW CO centrifugation tubes from Sartorius at full speed and 8° C.

TABLE 2

Summary of the characteristics of the different immobilization resins from Purolite Lifetech and the corresponding immobilization buffers.

| Purolite Lifetech Resin | Type | Immobilization type | Comment | Immobilization buffer |
|---|---|---|---|---|
| ECR8806 | Octadecyl methacrylate | Adsorption | For organic solvents | $PP_i$ buffer, 20 mM, pH 7.5 |
| ECR8285 | Epoxy/butyl methacrylate | Covalent (hydrophobic) | Aqueous/biphasic systems | $PP_i$ buffer, 0.5M, pH 7.5 |

Protein Concentration

The protein concentration in the samples was determined using the Bradford Assay (Bio-Rad; Art: 5000006). The Bradford solution was diluted 1:5 with $dH_2O$. The samples (5 µL) were pipetted in the wells of a transparent 96-well microtiter plate and Bradford solution (200 µL) was added. BSA standards with concentrations of 0.0625 to 2 mg/mL BSA and a blank sample were measured as well. All determinations were made in duplicates. After incubation of at least 5 min the absorbance at 595 nm was measured with a plate reader (with a 5 sec shaking period before measurements).

Immobilization

After buffer exchange, the protein solutions were concentrated by centrifugation using Vivaspin 20, 10.000 MW CO centrifugation tubes until the desired protein concentration of at least 10 mg/mL was reached.

Immobilization on ECR8285 by covalent binding: The beads (100 mg) were filled into a weighed 1.5 mL tube and washed four times with washing buffer (100 µL, 10 mM PPi, pH 7.5). Protein solution (5 mg protein in 600 µL immobilization buffer 0.5 M PPi, pH 7.5) was added to the washed beads and incubated for 18 hours at 50 rpm on a spinning wheel and for 20 h on the bench at room temperature. After washing the beads two times with washing buffer (100 µL, 10 mM PPB, pH 7.5), once with washing buffer containing 0.5 M NaCl (100 µL) for desorption of non-covalently bound proteins and one last time with washing buffer (100 µL), the enzyme beads were frozen at −80° C. for 1 h. The tubes were opened and placed in the lyophilizator for 24 h at −40° C. with 50 µbar vacuum. Subsequently, they were stored in the fridge and tested for the target amidation reaction with L-proline.

Initial procedure: At the beginning, the beads were filtered by vacuum filtration to remove excess water after immobilization and washing of the beads. Since a too high water content of the beads turned out to reduce amide formation drastically, beads were consequently lyophilized instead of vacuum filtration.

Immobilization on ECR8806 by adsorption: The beads (100 mg) were filled into a weighed 1.5 mL tube and washed twice with washing buffer (120 µL, 10 mM PPi, pH 7.5). Protein solution (5 mg protein in 600 µL immobilization buffer, 20 mM PPi, pH 7.5) was added to the washed beads and incubated for 24 hours at 50 rpm at room temperature on a spinning wheel. After washing the beads once with washing buffer (150 µL, 10 mM PPB, pH 7.5), the enzyme beads were frozen at −80° C. for 1 h. The tubes were opened and placed in the lyophilizator for 24 h at −40° C. with 50 pbar vacuum. Subsequently, they were stored in the fridge at 4° C. and tested for the target amidation reaction with L-proline.

The immobilization supernatant and the wash fractions were collected in a pre-weighed tube and the remaining protein concentration was measured, to determine the immobilization efficiency.

The invention claimed is:

1. A process for biocatalytic amidation of non-protected amino acids comprising the step of contacting a non-protected amino acid with an ammonia source in the presence of an organic solvent and a lipase enzyme, wherein the non-protected amino acid is L-proline, wherein the lipase is *Candida antarctica* lipase B (CalB) or a variant thereof, wherein the CalB variant has the amino acid substitutions T57A/A89T/G226R/R168K with reference to the numbering of SEQ ID NO: 1, and wherein the ammonia source is selected from the group consisting of ammonia, ammonium carbamate, ammonium carbonate, ammonium formate, and ammonium benzoate, and any mixtures thereof.

2. The process according to claim 1, wherein the lipase is immobilized.

3. The process according to claim 1, wherein the organic solvent is selected from the group consisting of dioxane, 2-methyl-2-butanol, t-butanol, and an ionic liquid.

4. The process according to claim 1, wherein the process is carried out at a temperature in the range of 60 to 80° C.

5. The process according to claim 1, wherein the organic solvent comprises the ammonia source.

6. The process according to claim 1, wherein the contacting step further comprises water in an amount below 1.0 v/v %, or below 0.5 v/v %.

7. The process according to claim 1, wherein the process is performed in batch or continuous mode.

8. The process according to claim 7, wherein the non-protected amino acid in the batch mode is provided in an amount of 0.01-1.0% w and the lipase enzyme is provided in an amount of 0.01-1.0% w.

* * * * *

SEQUENCE LISTING

```
<160> NUMBER OF SEQ ID NOS: 1

<210> SEQ ID NO 1
<211> LENGTH: 317
<212> TYPE: PRT
<213> ORGANISM: Artificial Sequence
<220> FEATURE:
<223> OTHER INFORMATION: T57A/A89T/G226R/R168K

<400> SEQUENCE: 1

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
        35                  40                  45

Asp Ser Asn Trp Ile Pro Leu Ser Ala Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Thr Leu Tyr Ala Gly Ser Gly Asn
```

-continued

```
                    85                  90                  95
Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
            130                 135                 140

Asp Ala Leu Ala Val Ser Ala Pro Ser Val Trp Gln Gln Thr Thr Gly
145                 150                 155                 160

Ser Ala Leu Thr Thr Ala Leu Lys Asn Ala Gly Gly Leu Thr Gln Ile
            165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Asp His
            210                 215                 220

Ala Arg Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
            245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
            275                 280                 285

Pro Lys Gln Asn Cys Glu Pro Asp Leu Met Pro Tyr Ala Arg Pro Phe
            290                 295                 300

Ala Val Gly Lys Arg Thr Cys Ser Gly Ile Val Thr Pro
305                 310                 315
```